(12) United States Patent
Nachbaur

(10) Patent No.: US 8,476,336 B2
(45) Date of Patent: Jul. 2, 2013

(54) OPHTHALMOLOGIC COMPOSITION AND OPHTHALMOLOGIC LENS

(75) Inventor: Juergen Nachbaur, Berlin (DE)

(73) Assignee: Acri.Tec GmbH, Hennigsdorf (DE)

( * ) Notice: Subject to any disclaimer, the term of this patent is extended or adjusted under 35 U.S.C. 154(b) by 412 days.

(21) Appl. No.: 12/640,952

(22) Filed: Dec. 17, 2009

(65) Prior Publication Data

US 2010/0160482 A1    Jun. 24, 2010

(30) Foreign Application Priority Data

Dec. 18, 2008 (DE) .......................... 10 2008 063 742

(51) Int. Cl.
| | |
|---|---|
| G02B 1/04 | (2006.01) |
| G02C 7/02 | (2006.01) |
| G02C 7/00 | (2006.01) |
| G02C 7/04 | (2006.01) |
| C08F 8/30 | (2006.01) |
| C07D 295/00 | (2006.01) |
| C07D 295/04 | (2006.01) |
| C07C 69/52 | (2006.01) |
| C07C 211/00 | (2006.01) |

(52) U.S. Cl.
USPC ............... 523/106; 351/159.01; 351/159.02; 525/329.9; 548/400; 548/570; 548/577; 548/578; 560/221; 564/441

(58) Field of Classification Search
USPC ......................................................... 523/106
See application file for complete search history.

(56) References Cited

U.S. PATENT DOCUMENTS 5,334,710 A    8/1994  Ahlheim et al.
2001/0052156 A1 * 12/2001  Bittner et al. ..................... 8/405

FOREIGN PATENT DOCUMENTS

| DE | 69318996 T2 | 10/1998 |
| WO | WO 0079312 A1 * | 12/2000 |
| WO | 2006/063139 A2 | 6/2006 |
| WO | 2007/147599 A1 | 12/2007 |

OTHER PUBLICATIONS

Computer generated English translation of WO 2007/147599 A1, Dec. 27, 2007, Nachbaur et al.*

* cited by examiner

*Primary Examiner* — Peter F Godenschwager
*Assistant Examiner* — David Karst
(74) *Attorney, Agent, or Firm* — Fitch, Even, Tabin & Flannery LLP

(57) ABSTRACT

The invention relates to an ophthalmologic composition including a dye of the general formula I

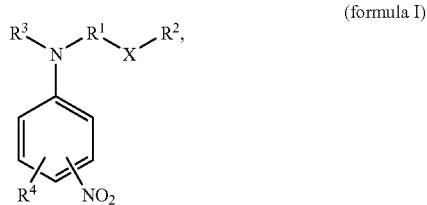

(formula I)

in which $R^1$=substituted or unsubstituted hydrocarbon radical, $R^2$=substituted or unsubstituted hydrocarbon radical with at least one polymerizable double bond, $R^3$=H or substituted or unsubstituted hydrocarbon radical, $R^4$=H, electron-withdrawing substituent or substituted or unsubstituted hydrocarbon radical and X=O, S, NH or $NR^5$, wherein $R^5$ is a substituted and/or unsubstituted hydrocarbon radical. Moreover, the invention relates to another ophthalmologic composition and an ophthalmologic lens.

9 Claims, No Drawings

OPHTHALMOLOGIC COMPOSITION AND OPHTHALMOLOGIC LENS

CROSS-REFERENCE TO RELATED APPLICATION

This application claims foreign priority to German Patent Application No. 10 2008 063 742.4, filed Dec. 18, 2008, which is hereby incorporated herein by reference in its entirety.

TECHNICAL FIELD

The invention relates to an ophthalmologic composition as well as an ophthalmologic lens.

PRIOR ART

It is known that violet light, i.e. light in the wavelength range between about 400 and 430 nm, plays a distinct role in the age-related macular degeneration. Therein, a group of diseases of the human and animal eye is understood by macular degeneration, which is associated with a gradual functional loss of the tissues located in the eye. The origin of the disease is the circumstance that the irradiation of violet light results in an accumulation of molecular waste (lipofuscin). In further consequence, this lipofuscin results in formation of so-called druses in turn inducing the macular degeneration, which can result in complete blindness. For this reason, violet light is considered phototoxic.

Furthermore, it is known that blue light, i.e. light in the wavelength range between about 450 and 500 nm, is of great importance for the vision at reduced lighting conditions, in particular for the scotopic and mesopic vision. Herein, the visual pigment rhodopsin occurring in the retin a of the eye plays an important role. Therein, rhodopsin, which belongs to the group of the G-protein coupled receptors, is localized in the photoreceptors (retinal rods) of the retina. Incidence of light results in isomerization of the retinal bound by the rhodopsin (11-cis-retinal->all-trans-retinal).

Ophthalmologic lenses are known from the prior art in various configurations. As intraocular lenses (IOLs), they are usually implanted after removing the natural lens (aphakia) or in case of defective visions. IOLs, which usually include an optic and a non-optic (haptic) part, are differentiated based on the ophthalmologic composition used for their manufacture among other things. In particular, one differentiates between IOLs manufactured from an acrylate or methacrylate material and IOLs manufactured from silicone material. Furthermore, IOLs can be formed one-piece or multi-piece. In one-piece intraocular lenses, the optic and non-optic parts are composed of a single material. In multi-piece IOLs, the optic and the non-optic parts can be composed of different materials. The non-optic parts are also referred to as haptic parts and serve for attachment. Alternatively, the ophthalmologic lenses can also be formed as contact lenses, which are accordingly only designed for temporary continuance on the eye.

In order to prevent damage to the different tissues in the eye, the ophthalmologic lenses or the ophthalmologic compositions used for their manufacture usually include a dye as an absorber, which is to absorb violet light as largely as possible. In case of a configuration of the lens as an intraocular lens (IOL), the dye is in particular provided in the optic part thereof.

However, dyes for intraocular lenses (IOLs) on the market absorb only partially in particular in the violet light range. With respect to order of magnitude, 25% to 35% of the phototoxic light passes the lens material provided with conventional dyes. Additionally, the known dyes are each only suitable for one lens material type, such that they are usable either for ophthalmologic compositions based on acrylate/methacrylate or for ophthalmologic compositions based on silicone.

Conversely, the dye or the ophthalmologic lens provided with it should absorb blue light as little as possible in order to be able to ensure maximum light irradiation and thus an optimum mesopic vision.

However, dyes for IOLs on the market only have a transmission of about 70% to 75% in this wavelength range (e.g. at 475 nm).

PRESENTATION OF THE INVENTION

The object of the present invention is to provide an ophthalmologic lens comprising a dye, which is usable more flexibly and at least largely absorbs violet light in the wavelength range up to about 430 nm, however, is at least largely transparent to blue light in the wavelength range from about 450-460 nm.

According to the invention, this object is solved by an ophthalmologic composition according to claim 1 an ophthalmologic composition according to claim 6 as well as an ophthalmologic lens according to claim 14. Advantageous configurations with convenient developments are specified in the respective dependent claims.

The invention provides an ophthalmologic composition, which is more flexibly usable and at least largely absorbs violet light in the wavelength range up to about 430 nm, however is at least largely transparent to blue light in the wavelength range from about 450-460 nm, by comprising a dye of the general formula I. In particular, a chemical composition or preparation for the opthamology is to be understood by an ophthalmologic composition.

The dye, which at least largely absorbs violet light in the wavelength range up to about 430 nm, however, is at least largely transparent to blue light in the wavelength range from about 450-460 nm, has the general formula I

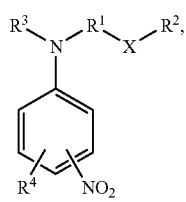

(formula I)

in which:

$R^1$=substituted or unsubstituted hydrocarbon radical;

$R^2$=substituted or unsubstituted hydrocarbon radical with at least one polymerizable double bond;

$R^3$=H or substituted or unsubstituted hydrocarbon radical;

$R^4$=H or substituted or unsubstituted hydrocarbon radical; and

X=O, S, NH or $NR^5$, wherein $R^5$ stands for a substituted and/or unsubstituted hydrocarbon radical. Therein, basically, all of the enantiomers, diastereomers and racemic mixtures of the general formula I are to be considered co-disclosed. In other words, the yellow dye of the general formula I is a polymerizable monomer with a nitroaniline group as an essential structural element, which is particularly flexibly usable for different polymer materials. On the one hand, the dye absorbs violet light, however, on the other hand, it is at least largely transparent to blue light. In this manner, in particular in use of the dye for ophthalmologic compositions or for ophthalmologic lenses, an advantageous macular protection of the eye of a patient is ensured with good mesopic vision at the same time.

In an advantageous development of the invention it is provided that in the dye of the general formula I, $R^2$ includes a vinyl and/or allyl and/or (meth)acryl radical as hydrocarbon radical with at least one polymerizable double bond. Hereby, the dye can be covalently incorporated into silicone-based or in acrylate or methacrylate-based polymers in particularly flexible manner depending on its respective purpose of use.

Therein, basically, a weight proportion of at least 51% of the entire polymer or of an entire composition is to be understood by a basis in the context of the present invention. Preferably, the proportion of the basis is greater than 90%, in particular greater than 95%, in particular greater than 98%.

Further advantages arise if $R^3$ is a radical without polymerizable double bond, in particular without vinyl and/or allyl and/or (meth)acryl group. Hereby, it is ensured that the dye has only one polymerizable group and accordingly does not have any cross-linking characteristics. This allows a particularly simple incorporation in different polymer materials, however, without fundamentally changing the mechanical characteristics thereof.

In another development, it has proven advantageous if $R^1$ and/or $R^2$ and/or $R^3$ and/or $R^4$ and/or $R^5$ includes a branched and/or unbranched alkyl and/or aryl radical with up to 30 atoms selected from C, H, Si, O, N, S, P, F, Cl, Br as the hydrocarbon radical. This allows a particularly flexible adaptability of the mechanical, chemical and optical characteristics of the dye to different profiles of requirement.

Therein, in further development, it has proven advantageous if the dye has the structure

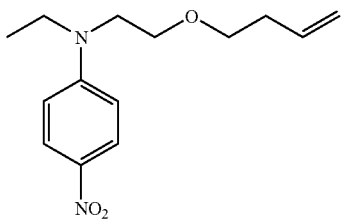 [SMILES: C=CCCOCCN(CC)c1ccc([N+](=O)[O-])cc1]

with:
$R^1=C_2H_4$, $R^2=C_4H_7$, $R^3=C_2H_5$, $R^4=H$ and $X=O$. Hereby, the dye is particularly well suited for ophthalmologic compositions based on silicone, and can be polymerized for example together with siloxanes having reactive groups as terminal chain link. Suitable siloxanes in particular include H-siloxanes.

Alternatively, it has proven advantageous if the dye has the structure

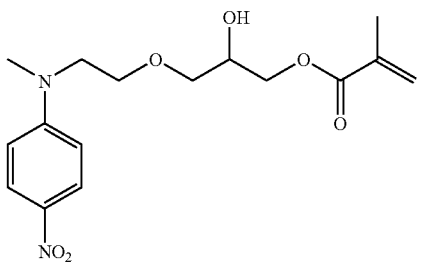 [SMILES: C=C(C)C(=O)OCC(O)COCCN(C)c1ccc([N+](=O)[O-])cc1]

with:
$R^1=C_5H_{10}O_2$, $R^2=C_4H_5O$, $R^3=CH_3$, $R^4=H$ and $X=O$. Hereby, the dye is particularly well suited for ophthalmologic compositions based on acrylate and/or methacrylate and can be polymerized for example together with hydrophobic and/or hydrophilic acrylate/methacrylate monomers. Basically, an acrylate group can be provided instead of the shown methacrylate group.

In another advantageous development of the invention, it is provided that at 20° C. the dye has a transmission degree of at most 0.07, preferably of at most 0.05, in the wavelength range between 400 nm and 430 nm, and/or a transmission degree of at least 0.25, preferably of at least 0.30, in the wavelength range between 450 nm and 475 nm, and/or a transmission degree of at least 0.80, preferably of at least 0.90, in the wavelength range between 490 nm and 550 nm. Preferably, the transmission spectrum of the dye has a sharp "cut-off" at about 430 nm, i.e. at 430 nm±10 nm. This means that the transmission of the dye increases as steeply as possible from a low transmission degree in the wavelength range up to about 430 nm from about 450-475 nm, i.e. from 450-475 nm±10 nm.

An ophthalmologic composition according to another aspect of the invention, which is more flexibly usable and largely absorbs violet light in the wavelength range up to about 430 nm, however, is at least largely transparent to blue light in the wavelength range from about 450-460 nm, comprises a dye, which has the general formula II

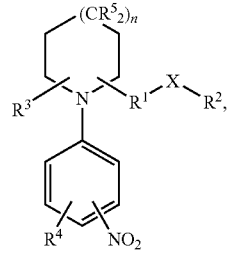

(formula II)

in which:
$R^1$=substituted or unsubstituted hydrocarbon radical;
$R^2$=substituted or unsubstituted hydrocarbon radical with at least one polymerizable double bond;
$R^3$=H or substituted or unsubstituted hydrocarbon radical;
$R^4$=H or substituted or unsubstituted hydrocarbon radical;
$R^5$=H and/or substituted and/or unsubstituted hydrocarbon radical;

n=1, 2, 3, if $R^2$ includes a (meth)acryl radical; or n=0, 1, 2, 3, if $R^2$ does not include any (meth)acryl radical; and $X=O$, S, NH or $NR^6$, wherein $R^6$ stands for a substituted and/or unsubstituted hydrocarbon radical. Therein, fundamentally, all of the enantiomers, diastereomers and racemic mixtures of the general formula II are to be considered co-disclosed. In other words, the yellow dye of the general formula II is a polymerizable monomer with a nitroaniline group and a saturated ring structure as the essential structural elements, which is particularly flexibly usable for different polymer materials. On the one hand, the dye absorbs violet light, however, on the other hand, it is at least largely transparent to blue light. In this manner, in particular in use of the dye for ophthalmologic compositions or for ophthalmologic lenses, an advantageous macular protection of the eye of a patient is ensured with good mesopic vision at the same time.

In an advantageous development of the invention, it is provided that in the dye of the general formula II, $R^2$ includes a vinyl and/or allyl and/or (meth)acryl radical as the hydrocarbon radical with at least one polymerizable double bond. Hereby, the dye can be covalently incorporated into silicone-based or into acrylate or methacrylate-based polymers in particularly flexible manner depending on its respective purpose of use.

Further advantages arise if $R^3$ is a radical without polymerizable double bond, in particular without vinyl and/or allyl and/or (meth)acryl group. Hereby, it is ensured that the dye only has one polymerizable group and accordingly does not have any cross-linking characteristics. This allows a particularly simple incorporation into different polymer materials, however, without fundamentally changing the mechanical characteristics thereof.

Further advantages arise by $R^1$ and/or $R^2$ and/or $R^3$ and/or $R^4$ and/or $R^5$ including a branched and/or unbranched alkyl and/or aryl radical with up to 30 atoms selected from C, H, Si, O, N, S, P, F, Cl, Br as the hydrocarbon radical. This allows a particularly flexible adaptability of the mechanical, chemical and optical characteristics of the dye to different profiles of requirement.

In another advantageous development, it has proven advantageous if the dye has the structure with:

$R^1=CH_2$, $R^2=C_4H_2$, $R^3$ and $R^4=H$, n=0 and $X=O$. Hereby, the dye is particularly well suited for ophthalmologic compositions based on silicone and can be polymerized for example together with siloxanes having reactive groups as terminal chain link. Suitable siloxanes in particular include H-siloxanes.

Alternatively, it has proven advantageous if the dye has the structure

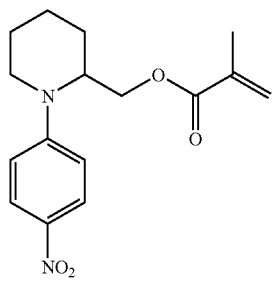

with:

$R^1=CH_2$, $R^2=C_4H_5O$, $R^3$ and $R^4=H$, n=1, $R^5=H$ and $X=O$. Hereby, the dye is particularly well suited for ophthalmologic compositions based on acrylate and/or methacrylate and can be polymerized for example together with hydrophobic and/or hydrophilic acrylate/methacrylate monomers. Basically, an acrylate group can be provided instead of the shown methacrylate group.

In another advantageous development of the invention, it is provided that at 20° C., the dye has a transmission degree of at most 0.07, preferably of at most 0.05, in the wavelength range between 400 nm and 430 nm, and/or a transmission degree of at least 0.25, preferably of at least 0.30, in the wavelength range between 450 nm and 475 nm, and/or a transmission degree of at least 0.80, preferably of at least 0.90, in the wavelength range between 490 nm and 550 nm. Preferably, the transmission spectrum of the dye has a sharp "cut-off" at about 430 nm, i.e. at 430 nm±10 nm. This means that the transmission of the dye increases as steeply as possible from a low transmission degree in the wavelength range up to about 430 nm from about 450-475 nm, i.e. from 450-475 nm±10 nm.

A further aspect of the invention relates to an ophthalmologic composition, which according to the invention is more flexibly usable and at least largely absorbs violet light in the wavelength range up to about 430 nm, however is at least largely transparent to blue light in the wavelength range from about 450-460 nm, by comprising a dye of the general formula I and/or a dye of the general formula II. The features and advantages thereof resulting from this are apparent from the previous descriptions and correspondingly apply to the ophthalmologic composition. In particular, a chemical composition or preparation for the opthamology is to be understood by an ophthalmologic composition.

Therein, it has proven advantageous if the dye is covalently incorporated in a polymer. This minimizes or render impossible an undesired release of the dye in many applications in particularly reliable manner.

Preferably, the ophthalmologic composition includes a monomer according to the following general formula III (general formula III)

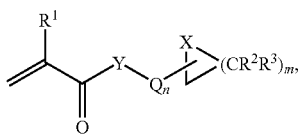

wherein $R^1$, $R^2$ and $R^3$ each independently of each other denote hydrogen or alkyl;

Y: denotes O or $NR^4$ with $R^4$ selected from hydrogen or alkyl;

X: denotes O, S, SO or $SO_2$;

Q: denotes a structural unit selected from $CHR^5$ or $(CHR^5CHR^6O)_iCH_2$, wherein $R^5$ and $R^6$ each independently of each other denote hydrogen or alkyl;

n and i independently of each other denote an integer between 1 and 10 and m denotes an integer between 2 and 6. With the aid of the monomer of the general formula III, ophthalmologic compositions or ophthalmologic lenses can be produced, which are particularly well suited for the so-called Micro Incision Cataract Surgery (MICS). This means that an implantation of a corresponding ophthalmologic lens by an incision of less than 2.0 mm, in particular of less than 1.7 mm, is possible.

In an advantageous development it is provided that the monomer of the general formula III has the following structure:

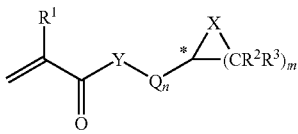

Hereby, the monomer additionally has improved mechanical characteristics besides the previously explained advantages, if it is incorporated into an ophthalmologic lens.

In a preferred embodiment, the radicals $R^1$, $R^2$, $R^3$, $R^4$, $R^5$ and $R^6$ are each independently of each other selected from unbranched and/or branched alkyl groups with preferably 1, 2, 3, 4, 5, 8, 7, 8, 9 and/or 10 carbon atoms. Further preferred, the radicals $R^1$, $R^2$, $R^3$, $R^4$, $R^5$ and $R^6$ are independently of each other a methyl group, ethyl group, n-propyl group, iso-propyl group, n-butyl group, iso-butyl group and/or tert-butyl group.

In a further preferred embodiment, the structural unit Q is a methylene group, and in a further preferred embodiment, the structural unit Q is a $-CH(CH_3)CH_2OCH_2-$ group.

In a further preferred embodiment, n and i are independently of each other 1, 2, 3, 4, 5, 8, 7, 8, 9 and/or 10. In a further preferred embodiment m is 2, 3, 4, 5 or 6.

In a further preferred embodiment, the radical $R^1$ is a methyl group if the structural unit Y is an O atom. It is further preferred that the radical $R^1$ represents hydrogen if the group Y is NH.

It is further preferred that the monomer of the general formula III has the following structure

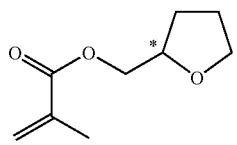

Therein, this monomer (tetrahydrofuran-2-yl)-methyl methacrylate is also known under the non-scientific name tetrahydrofurfuryl methacrylate (THFMA). Alternatively or additionally, herein, the positional isomer (tetrahydrofuran-3-yl)-methyl methacrylate can also be provided.

It can be provided that the ophthalmologic composition has a copolymer, wherein the copolymer includes:
a) based on the total weight of the copolymer, 20 to 95 percent by weight of structural units derived from at least one hydrophilic monomer, and
b) based on the total weight of the copolymer, 5 to 80 percent by weight of structural units derived from at least one monomer according to the general formula III

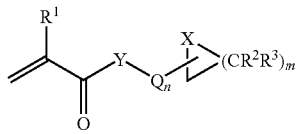

wherein $R^1$, $R^2$ and $R^3$ each independently of each other denote hydrogen or alkyl, Y: denotes O or $NR^4$ with $R^4$ selected from hydrogen or alkyl, X: denotes O, S, SO or $SO_2$, Q: denotes a structural unit selected from $CHR^5$ or $(CHR^5CHR^6O)_iCH_2$, wherein $R^5$ and $R^6$ each independently of each other denote hydrogen or alkyl, n and i independently of each other denote an integer between 1 and 10, and m denotes an integer between 2 and 6, and wherein the copolymer has a water content of 1 to 59 percent by weight based on the total weight of the copolymer. Therein, all stereoisomers and racemic mixtures of the monomers a) and b) are fundamentally to be considered encompassed. In particular, the copolymer has improved characteristics if it is incorporated into an ophthalmic lens or used for producing such a lens. Such an ophthalmic lens and in particular an intraocular lens can be better folded in implantation such that the surgical procedure requires a particularly small incision before introduction of the intraocular lens into the eye. Therefore, the lens is particularly well suited for the so-called Micro Incision Cataract Surgery (MICS). In addition, the compatibility of such a copolymer in the eye is very good.

It is further preferred that based on the total weight of the copolymer, 30 to 79 percent by weight of structural units are derived from the at least one hydrophilic monomer a) and further preferred 50 to 79 percent by weight of structural units are derived from the at least one hydrophilic monomer a) in the copolymer.

In a further preferred embodiment, based on the total weight of the copolymer, 10 to 79 percent by weight, in particular 21 to 60 percent by weight, preferably 21 to 50 percent by weight and further preferred 21 to 35 percent by weight in the copolymer are derived from the at least one monomer b) according to the general formula III. In particular, in the copolymer, 10 to 35 percent by weight based on the total weight of the copolymer can also be derived from the at least one monomer b) according to the general formula III.

Preferably, the copolymer has a water content of 2 to 50 percent by weight, further preferred of 5 to 40 percent by weight, and particularly preferred between 10 and 30 percent by weight based on the total weight of the copolymer.

The proportions of structural units derived from monomers specified within the scope of the disclosure relate to the total weight of the copolymer, and these individual proportions and the water content are preferably to be selected such that 100 percent by weight are obtained in total. In case that further ingredients are contained in the copolymer, these weight proportions and the water content are to be selected such that a total weight of the copolymer inclusive of the further ingredients results in 100 percent by weight.

It is further preferred that the hydrophilic monomer a) is a monomer of the general formula IV

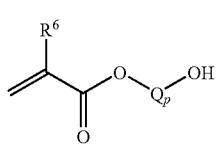

(general formula IV)

wherein

Q: denotes a structural unit selected from $CHR^7$ or $(CHR^7CHR^8O)_kCH_2$, wherein $R^7$ and $R^8$ each independently of each other denote hydrogen or alkyl, and p and k independently of each other denote an integer between 1 and 10. Herein too, all of the stereoisomers and racemic mixtures are to be considered encompassed.

In a preferred embodiment, the radicals $R^6$, $R^7$ and $R^8$ are each independently of each other selected from unbranched and/or branched alkyl groups with preferably 1, 2, 3, 4, 5, 8, 7, 8, 9 and/or 10 carbon atoms. Further preferred, the radicals $R^6$, $R^7$ and $R^8$ are each independently of each other a methyl group, ethyl group, n-propyl group, iso-propyl group, n-butyl group, iso-butyl group and/or tert-butyl group. For $R^6$ it is particularly preferred independently thereof that $R^6$ is methyl or H.

For some cases it can be preferred that the copolymer does not contain any structural units that are derived from at least one alkoxyalkyl methacrylate monomer and/or one alkoxyalkyl acrylate monomer.

In a further preferred embodiment k and p are independently of each other 1, 2, 3, 4, 5, 8, 7, 8, 9 and/or 10.

In a still further preferred embodiment, the hydrophilic monomer of the general formula IV is hydroxyethyl methacrylate (HEMA) and/or hydroxypropyl methacrylate (HPMA). Alternatively or additionally, glycerine monomethacrylate can be provided as the hydrophilic monomer.

It is further preferred that the monomer b) of the general formula III has the following structure

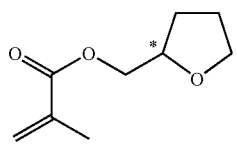

Therein, this monomer (tetrahydrofuran-2-yl)methyl methacrylate is also known under the non-scientific name tetrahydrofurfuryl methacrylate (THFMA). Alternatively or additionally, herein, the positional isomer (tetrahydrofuran-3-yl)methyl methacrylate can also be provided.

In a preferred embodiment, the monomers of the general formula III and/or IV are in enantiomerically pure form. Alternatively preferred, the monomers of the general formula III and/or IV can be present as a racemic mixture.

In a further preferred embodiment, the copolymer includes at least one or more cross-linkers. As suitable cross-linkers, vinyl monomers or oligomers can be provided which have two or more polymerizable groups. Hereby, the copolymer can be specifically three-dimensionally cross-linked and the cross-linking degree can be adjusted depending on the respective purpose of application in optimum manner. For example, ethylene glycol dimethacrylate (EGDMA), trimethylolpropanetri(meth)acrylate, 1,3-glycerinedi(meth)acrylate and/or butanedioldi(meth)acrylate can be provided as cross-linkers.

In a further preferred embodiment, the ophthalmologic composition contains an UV absorber. Therein, organic or anorganic compounds are to be understood by UV absorber, which at least largely and preferably quantitatively absorb radiation in a wavelength range between 200 nm and 400 nm. A biocompatible UV light protection agent is provided as UV absorber, for which coumarin derivatives, which are optionally linked to one or more acryl or methacryl functions via acryl spacers can be used.

In a further advantageous development of the invention, it is provided that the UV absorber is a compound of the general formula V, in which a coumarin base body is linked to one or more acryl or methacryl radicals via different spacers:

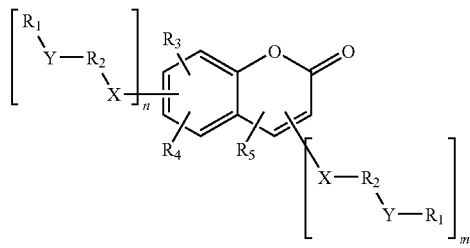

(general formula V)

wherein $R_1$: denotes acryl and/or methacryl radicals

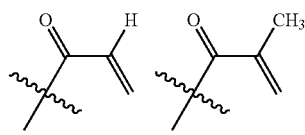

$R_2$: denotes organic branched and/or unbranched alkyl and/or aryl substituents with up to 30 atoms selected from C, H, Si, O, N, P, S, F, Cl, Br, $R_3$, $R_4$ and $R_5$: denote H and/or organic branched and/or unbranched alkyl and/or aryl substituents with up to 30 atoms selected from C, H, Si, O, N, P, S, F, Cl, Br, X, Y: denote O, S, NH or $NR^6$, wherein $R^6$ is an organic branched and/or unbranched alkyl and/or aryl substituent with up to 30 atoms selected from C, H, Si, O, N, P, S, F, Cl, Br, and n is an integer between 0 and 2 as well as m is 0 or 1, wherein the sum n+m is always greater than or equal to 1.

Herein too, all of the stereoisomers and racemic mixtures are to be considered encompassed. Examples for suitable structures according to formula V are:

structure 1

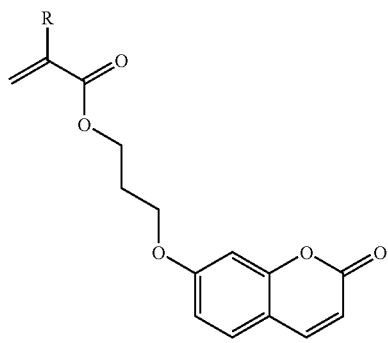

structure 2

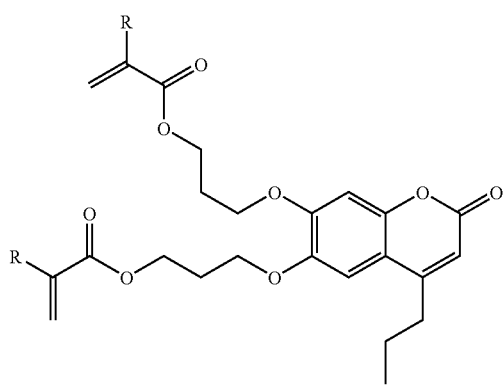

structure 3

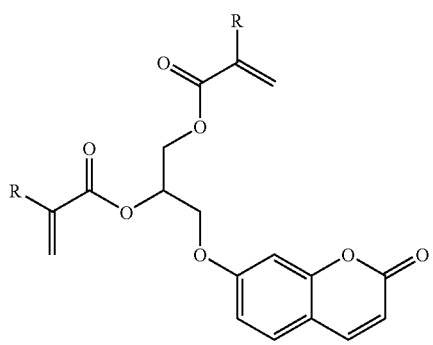

structure 4

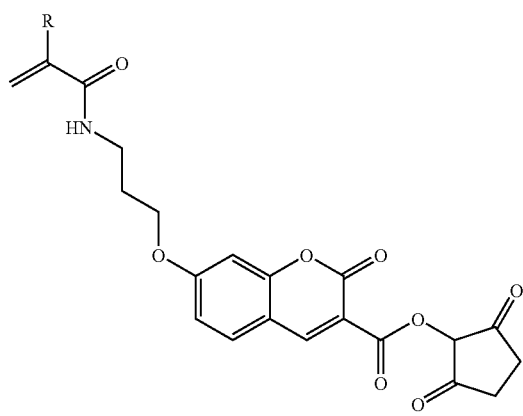

structure 5

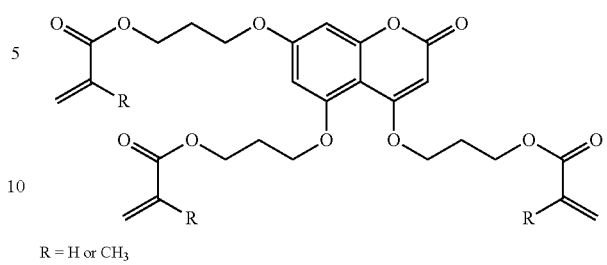

R = H or CH₃

UV absorbers, the basic structure of which is based on the structures 2, 3 or 5, have the additional advantage that they allow a quantitative incorporation into the lens material attributable to the presence of plural polymerizable terminal groups and moreover have cross-linking characteristics. Upon lens production, thus, in ideal case, the addition of an additional cross-linker can be omitted.

A preferred UV absorber is coumarin-7-propoxymethacrylate with n=1, m=0, X═O, $R_2$═$C_3H_6$, Y═O, $R_1$═methacryl radical, $R_3$═H, $R_4$═H, $R_5$═H with the structure:

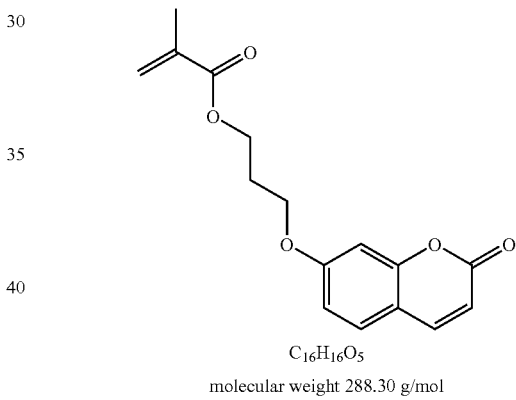

$C_{16}H_{16}O_5$ molecular weight 288.30 g/mol

The preparation of this compound is effected in two steps, wherein the 7-hydroxycoumarin is commercially available:

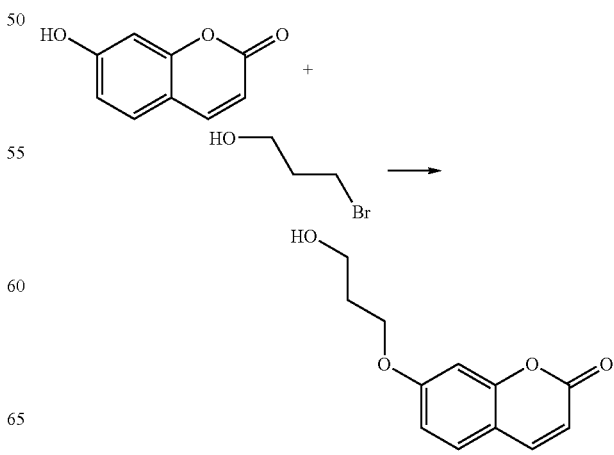

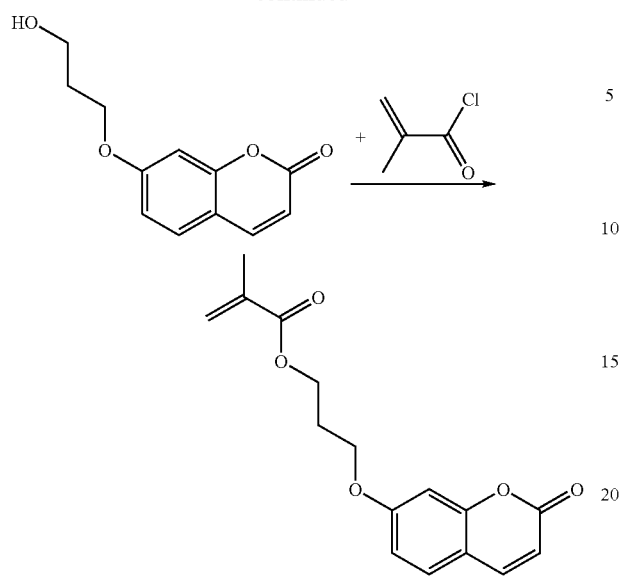

A further example of the UV absorber of the general formula V is the compound with n=2, m=0, X=O, $R_2$=$C_3H_6$, Y=O, $R_1$=acryl and/or methacryl radical, $R_3$=H, $R_4$=H, $R_5$=H in the general formula V, whereby the following structure results:

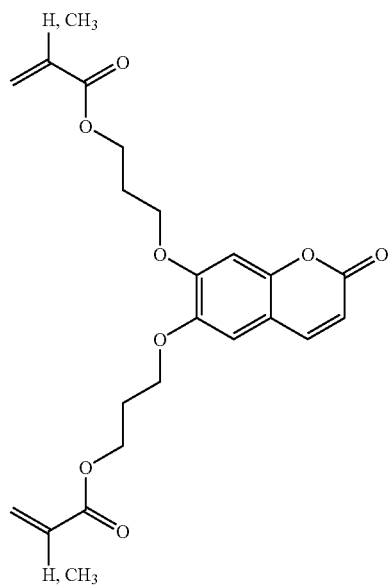

A further embodiment of an UV absorber is coumarin-6,7-dipropoxy methacrylate. This one too can be presented in a 2-step reaction analog to the coumarin-7-propoxy methacrylate in a simple synthetic way. The 6,7-dihydroxycoumarin required thereto is also commercially available. In this manner, a compound can be prepared, in which an additional methacrylate anchor group has been introduced. The attachment of this second anchor group via an alkoxy spacer has only a low influence on the spectral characteristics of the absorber, however, it allows using it also as a cross-linker in the production of the lens material.

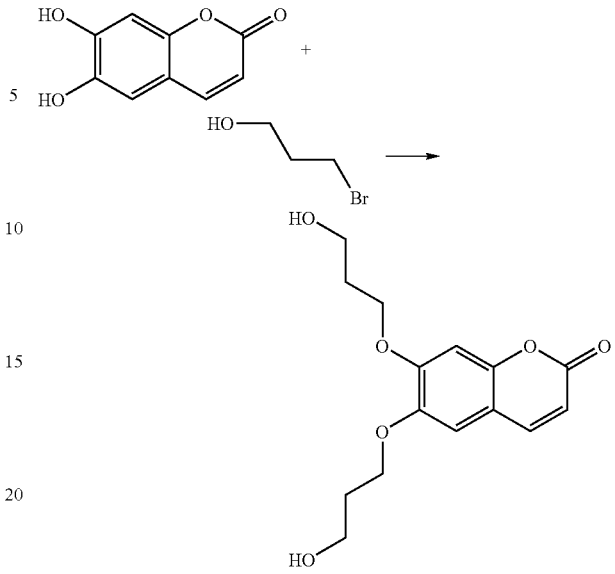

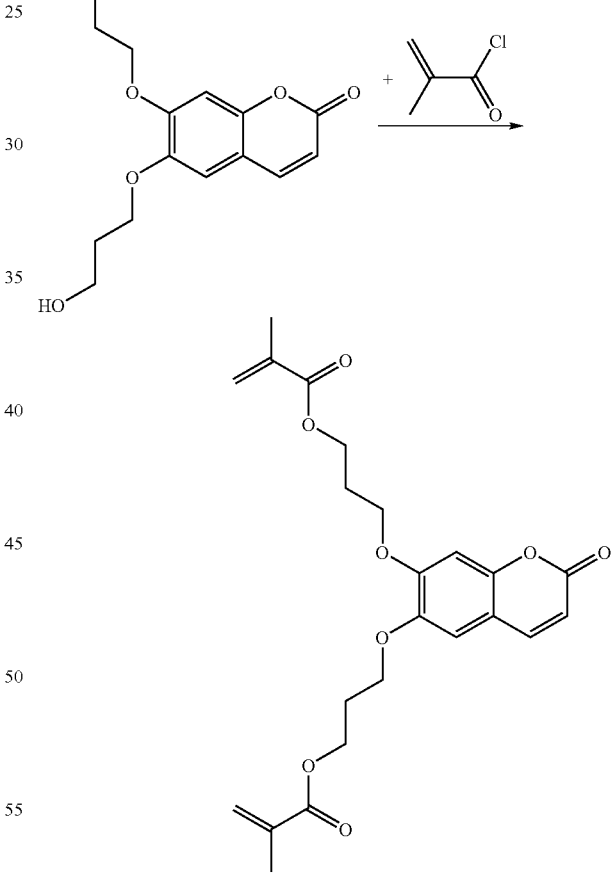

A further example of an UV absorber of the general formula V is a structure with n=1, m=0, X=O, $R_2$=—$CH_2$—CH($OR_1$)$CH_2$—, Y=O, $R_1$=acryl or methacryl radical, $R_3$=H, $R_4$=H, $R_5$=H.

A further possibility of producing an UV absorber with two anchor groups results from the use of a branched dihydroxy halide. If, in a first step, one reacts 7-hydroxycoumarin with commercially available 3-bromo-1,2-propanediol and one subsequently acrylates or methacrylates the developed alkoxydiol, one obtains a further bifunctional UV absorber.

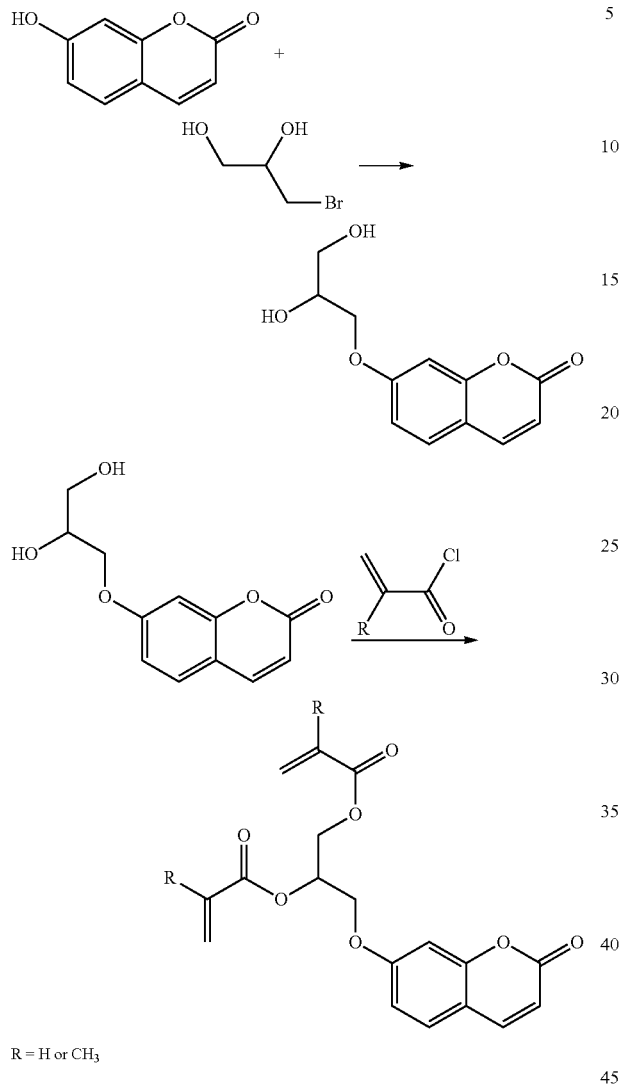

R = H or CH₃

A further example of an UV absorber of the general formula V is a structure with n=1, m=0, X=O, R²=-CH₂—CH(OR1)CH₂—, Y=O, R¹=methacryl radical, R³=H, R⁴=H, R⁵=H.

If one reacts 7-hydroxycoumarin not with acrylic acid or methacrylic acid, but with commercially available methacrylic glycidyl ester, thus, one obtains in a single reaction step a further UV filter, in which the coumarin basic body is separated from the methacrylate radical by an aliphatic chain. By subsequent esterification with methacryloyl chloride, a further methacrylate function can be introduced at the secondary alcohol group.

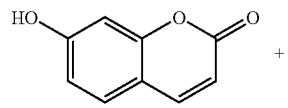

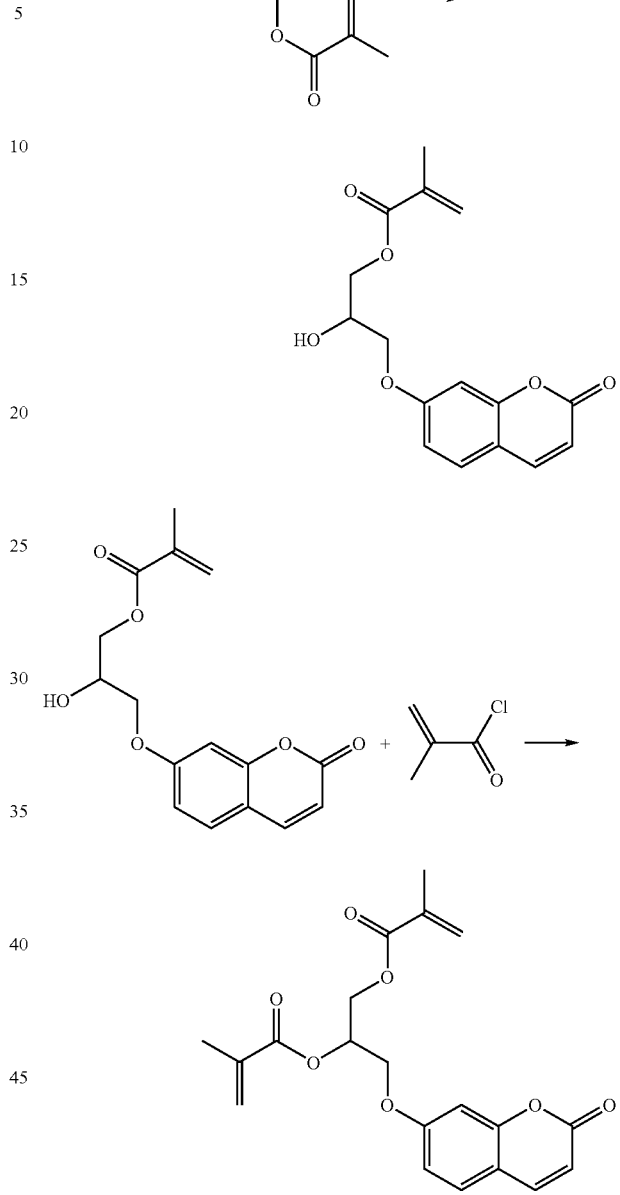

A further example of an UV absorber of the general formula V is a structure with n=1, m=0, X=O, R₂=C₃H₆, Y=O, R₁=acryl or methacryl radical, R₃=H, R₄=H, R₅=C₁₋₃H₇.

Here, R₅ is a propyl group having a weak inductive effect (+I effect). The introduction of an additional propyl group into the previously described preferred UV absorber can be accomplished synthetically without problems and modifies the spectral characteristics of the chromophore only to a minor degree. If one does not employ 7-hydroxycoumarin, but the also commercially available 7-hydroxy-4-propylcoumarin in the synthesis, one obtains a coumarin derivative after the methacrylation, which differs from the preferred UV absorber by only one propyl side chain.

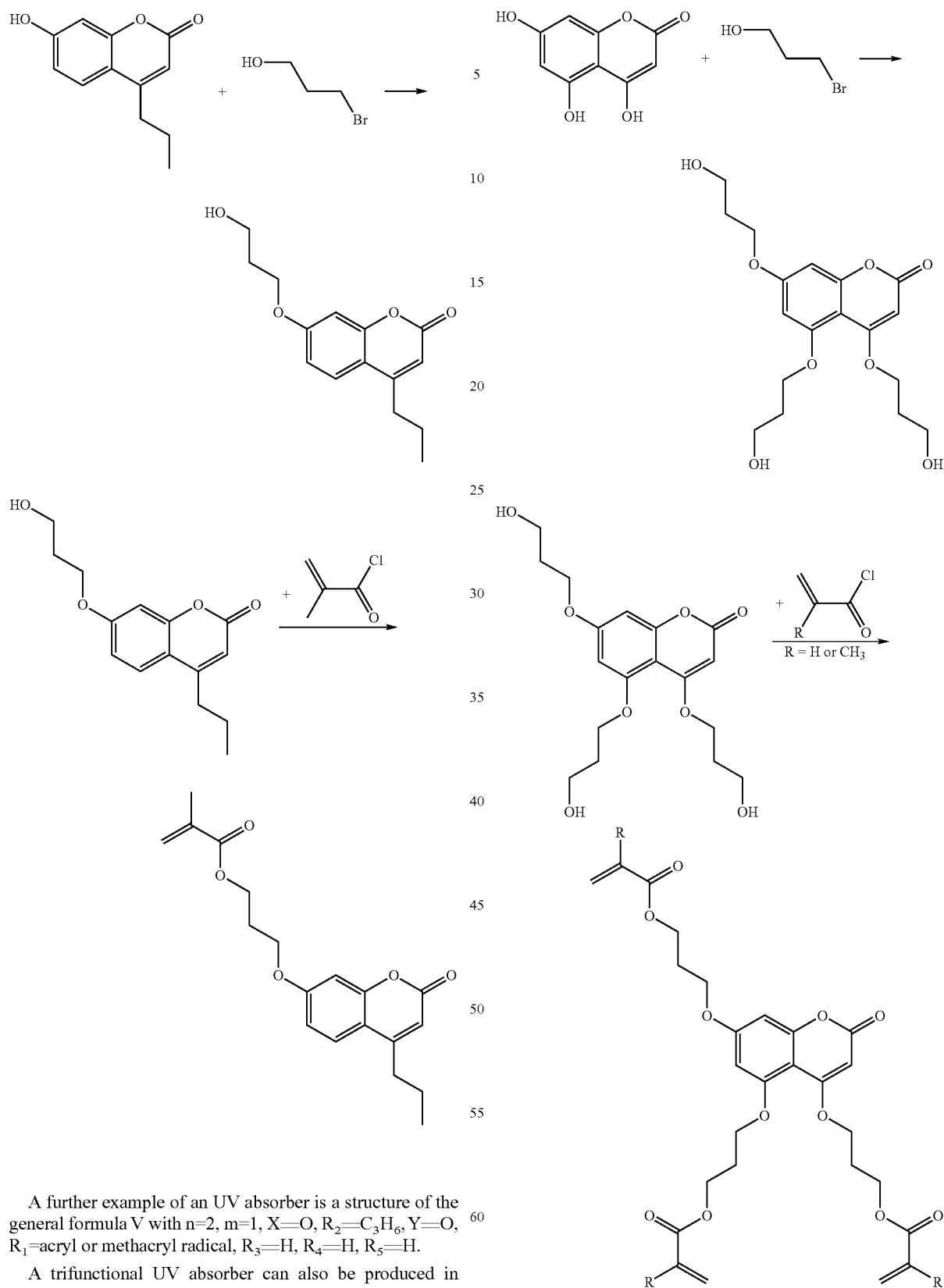

A further example of an UV absorber is a structure of the general formula V with n=2, m=1, X=O, R$_2$=C$_3$H$_6$, Y=O, R$_1$=acryl or methacryl radical, R$_3$=H, R$_4$=H, R$_5$=H.

A trifunctional UV absorber can also be produced in simple synthetic way. Starting from 4,5,7-trihydroxycoumarin, after the alkoxylation with 3-bromo-1-propanol and subsequent acrylation or methacrylation, one obtains an UV absorber of the general formula V with three anchor groups.

It can also be provided that the UV absorber is methacrylic-(2-[3-(2H-benzotriazol-2-yl)-4-hydroxyphenyl]ethyl ester).

The ophthalmologic composition can for example have a following component configuration:

| | |
|---|---|
| EOEMA (ethoxyethyl methacrylate) | 85-97 wt.-% |
| MMA (methyl methacrylate) | 0-15 wt.-% |
| EEEA (ethoxyethoxy ethyl acrylate) | 0-5 wt.-% |
| EGDMA (ethylene glycol dimethacrylate) | 0-0.7 wt.-% |
| UV absorber | 0.1-1.0 wt.-% |
| Violet absorber | 0.03-0.16 wt.-% |

Therein, the violet absorber is a dye of the formulas I and/or II or an advantageous implementation thereof.

In a further advantageous development of the invention, the ophthalmologic composition includes 50-90%, preferably 70-85%, particularly preferred 70-80% HEMA (hydroxyethyl methacrylate), 10-40%, preferably 16-40%, preferably 16-30% MMA (methyl methacrylate), 0.25-1.5%, preferably 0.4%-0.60, in particular 0.5% cross-linker, 0.01-0.3% radical initiator, 0.1-3.0%, preferably 0.70-0.80%, preferably 0.75% UV absorber and 0.02-0.3%, preferably 0.16-0.30% dye as violet absorber. Therein, the percent specifications basically stand for percent by weight. Preferably, the water content of the composition is between 20% and 35%, preferably between 24% and 30%.

In a further preferable implementation, the ophthalmologic composition has the following components:

| | |
|---|---|
| HEMA (hydroxyethyl methacrylate) | 50-85 wt.-% |
| EOEMA (ethoxyethyl methacrylate) | 30-40 wt.-% |
| THFMA (tetrahydrofurfuryl methacrylate) | 5-20 wt.-% |
| EGDMA (ethylene glycol dimethacrylate) | 0-0.7 wt.-% |
| UV absorber | 0.1-1.0 wt.-% |
| violet absorber | 0.03-0.16 wt.-% |

Therein, the violet absorber is a dye of the formulas I and/or II or an advantageous implementation thereof.

In a further implementation, the proportion of the THFMA can be greater than 20%, in particular up to 50%, wherein the proportion of the component HEMA can then be smaller than 50% and/or the proportion of EOEMA can be smaller than 30%. EOEMA can also be not present.

In all of the implementations, the percent by weight of the components are selected in the respective composition in total such that they result in 100%, wherein possibly also present radical initiators or their components incorporated in the polymer are encompassed.

A suitable cross-linker is for example EGDMA (ethylene glycol dimethacrylate). However, as a radical initiator optionally depending on the reaction temperatures—for example AIBN (azo-bis-(isobutyronitrile)) and/or V65 can also be provided.

The ophthalmologic composition has a high biocompatibility as well as a high peak refraction power (diopter). In addition, the ophthalmologic composition is particularly well suited for producing ophthalmologic lenses for small incision applications, in particular for MICS applications. Further, the ophthalmologic composition preferably has a water content between 20% and 35%, in particular between 24% and 30%.

A further aspect of the invention relates to an ophthalmologic lens, which according to the invention is more flexibly usable and at least largely absorbs violet light in the wavelength range up to about 430 nm, however is at least largely transparent to blue light in the wavelength range from about 450-460 nm, by including an ophthalmologic composition according to anyone of the preceding embodiments.

Hereby, the lens according to the invention disposes of a high refractive index as well as of a particularly good foldability with high biocompatibility, and basically can be formed one-piece or multi-piece. Therein, basically, it can be provided that the lens is exclusively composed of the ophthalmologic composition. Further features and the advantages thereof are apparent from the preceding description and correspondingly apply to the ophthalmologic lens, wherein the advantageous implementations of the ophthalmologic composition according to the above-mentioned aspect are in particular to be considered as advantageous implementations of the further ophthalmologic composition.

In an advantageous development of the invention, it has proven advantageous if the lens is formed as an intraocular lens. It can also be provided a configuration as a contact lens.

A further aspect relates to a use of a dye of the general formula I and/or of the general formula II and/or of an ophthalmologic composition according to anyone of the preceding embodiments for producing an ophthalmologic lens, in particular of a contact or intraocular lens, and/or of a medical implant, in particular of an eye implant. The features and advantages thereof resulting from this are apparent from the preceding descriptions and correspondingly apply to the use according to the invention.

Further features of the invention are apparent from the claims and the embodiments. The features and feature combinations mentioned above in the description as well as the features and feature combinations mentioned below in the embodiments are usable not only in the respectively specified combination, but also in other combinations or alone without departing from the scope of the invention.

PREFERRED IMPLEMENTATION OF THE INVENTION

Embodiment 1

In the first embodiment for a yellow dye of the general formula I, the following compound 1:

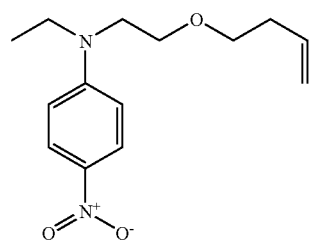

Compound 1: N-(2-(but-3-enyloxy)ethyl)-N-ethyl-4-nitrobenzeneamine with: $R^1=C_2H_4$, $R^2=C_4H_7$, $R^3=C_2H_5$, $R^4=H$ and $X=O$ is prepared. The synthesis of the compound 1 starts with the reaction of the commercially available 1-fluoro-4-nitrobenzene with the also commercially available 2-ethylaminoethanol according to the general reaction scheme

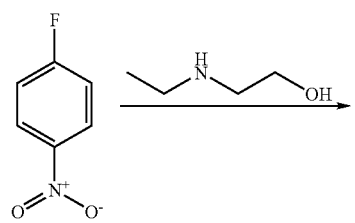

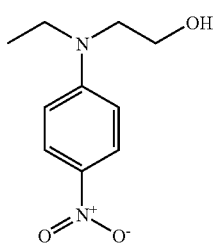

The obtained intermediate stage (1) (2-(ethyl(4-nitrophenyl)amino)ethanol) is subsequently reacted with p-toluenesulfonic acid chloride according to the general reaction scheme

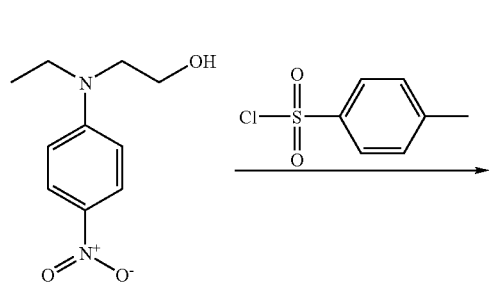

to the intermediate stage (2) [2-(ethyl(4-nitrophenyl)amino)ethyl-4-methylbenzenesulfonate]. The compound 1 with a polymerizable vinyl group is finally obtained by substitution of the intermediate stage (2) with 1-hydroxy-3-butene:

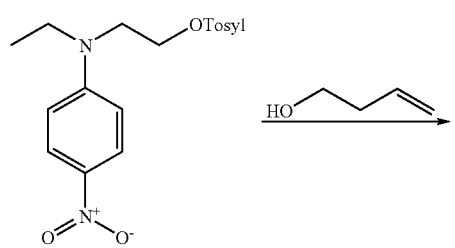

-continued

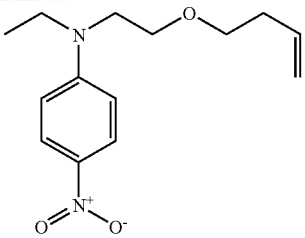 [SMILES: C=CCCOCCN(CC)c1ccc([N+](=O)[O-])cc1]

Embodiment 2

In the second embodiment for a yellow dye of the general formula II with a vinyl group, the compound 2

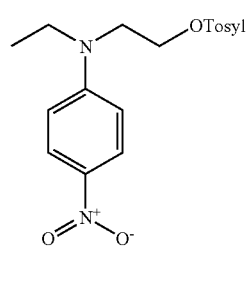

Compound 2: 2-((but-3-enyloxy)methyl)-1-(4-nitrophenyl)pyrrolidine with:

R$^1$=CH$_2$, R$^2$=C$_4$H$_2$, R$^3$ and R$^4$=H, n=0 and X=O is prepared. The synthesis of the compound 2 starts with the reaction of the commercially available (1-(4-nitrophenyl)pyrrolidine-2-yl)methanol with p-toluenesulfonic acid chloride to the intermediate product (1).

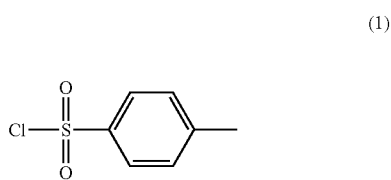

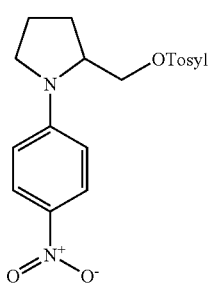

The compound 2, which includes a polymerizable vinyl group, is obtained by subsequent substitution of the intermediate product (1) with 1-hydroxy-3-butene:

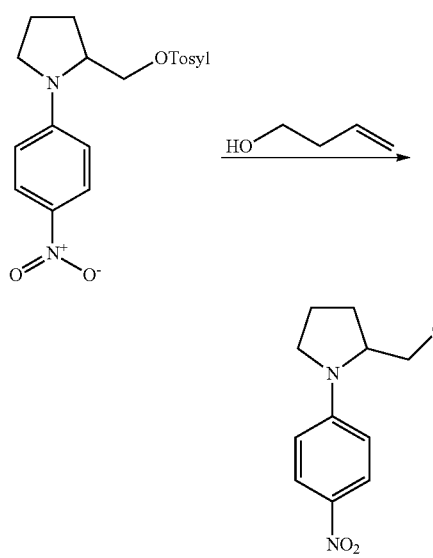

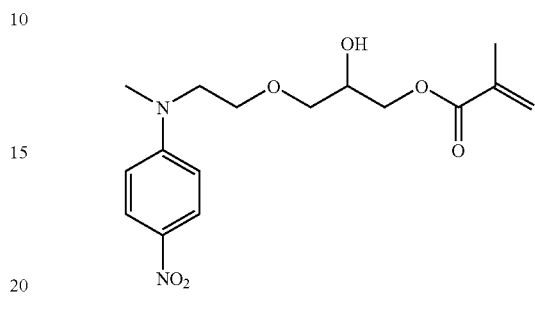

Detailed Description of Synthesis:

(S)-[1-(4-nitrophenyl)pyrrolidine-2-yl]methanol (11.5 g, 51.7 mmole), tetrabutylammonium-hydrogensulfate (TBAHS, 2.8 g, 8.2 mmole) and powdered sodium hydroxide (14.3 g, 357 mmole) are combined in 120 ml tetrahydrofuran (THF). Subsequently, at 5° C.-10° C. p-toluenesulfonic acid chloride (11.5 g, 60.3 mmole) is added to the mixture in portions within 10 minutes. The reaction mixture is stirred during 2 hours at 5° C.

For processing, the mixture is diluted with saturated sodium hydrogen carbonate solution (75 ml) and stirred for 10 minutes at room temperature. The phases are separated. The aqueous phase is extracted with dichloromethane (3×15 ml). The combined organic phases are dried with $Na_2SO_4$ and then filtrated. The volatile components of the filtrate are optionally completely removed in vacuo. There remains the yellow intermediate product (1) (toluene-4-sulfonic acid-(S)-1-(4-nitrophenyl)pyrrolidine-2-yl-methylester) (21.3 g, ca. 100%) as a solid, which can be used without further purification for the subsequent reaction. The intermediate product (1) (21.3 g, ca. 51.7 mmole), toluene (175 ml), 1-hydroxy-3-butene (26.2 g, 36.3 mmole), tetrabutylammonium hydrogen sulfate (5.2 g, 15.3 mmole) and 50-percent sodium hydroxide solution (70 g, 873 mmole) are combined. Then, the reaction mixture is stirred for 90 minutes at 65° C. to 70° C. For processing, the mixture is mixed with 65 ml of water. The phases are separated. The aqueous phase is extracted with dichloromethane (3×20 ml). The combined organic phases are dried with $Na_2SO_4$ and then filtrated. The volatile components of the filtrate can be completely removed in vacuo. The residue (brown oil, 21.6 g) is purified by column chromatography (solvent cyclohexane/ethyl acetate 11:1). The obtained yellow oil (8.58 g) can preferably be crystallized overnight. For fine purification, the product is twice recrystallized from methanol. The crystals are dissolved in methanol (50 ml) at room temperature. Subsequently, the solution is slowly cooled to −55° C. to −60° C. and then stirred for 10 minutes. The precipitated crystals are sucked off and washed with cold hexane (−75° C., 3×10 ml). This procedure was repeated once again. The compound 2 ((S)-2-but-3-enyloxymethyl-1-(4-nitrophenyl)pyrrolidine) is obtained as a yellow solid in a yield of 57% (8.20 g) with a melting point of 35-36° C. (HPLC purity 99.7%). However, it is to be emphasized that the synthesis does not have to be performed with enantiomerically pure educts and racemic mixtures can also be used.

Embodiment 3

In the third embodiment for a yellow dye of the general formula I with a methacrylate group, the copound 3

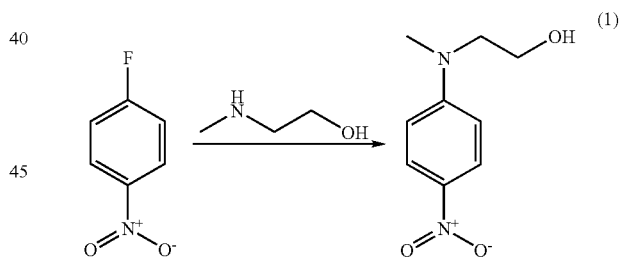

Compound 3: 2-hydroxy-3-(2-(methyl(4-nitrophenyl)amino)ethoxy)propyl Methacrylate with:

$R^1=C_5H_{10}O_2$, $R^2=C_4H_5O$, $R^3=CH_3$, $R^4=H$ and X=P.

is prepared. The synthesis of the compound 3 again starts with the reaction of the commercially available 1-fluoro-4-nitrobenzene with the commercially available 2-methylaminoethanol to the intermediate product (1) [2-(methyl(4-nitrophenyl)amino)ethanol].

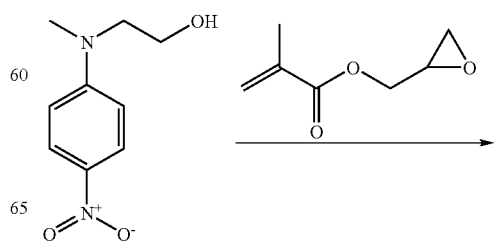

The obtained intermediate product (1) is subsequently reacted with methacrylic glycidyl ester to the compound 3:

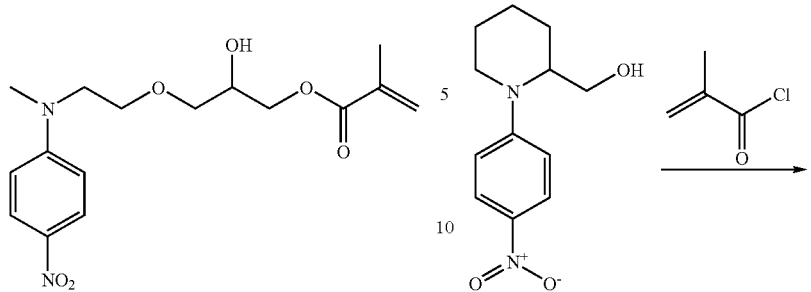

Embodiment 4

In the fourth embodiment for a yellow dye of the general formula II with a methacrylate group, the compound 4:

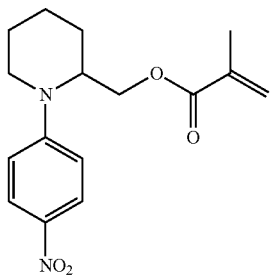

Compound 4:
(1-(4-nitrophenyl)piperidine-2-yl)methyl
Methacrylate with:

$R^1$=CH$_2$, $R^2$=C$_4$H$_5$O, $R^3$ and $R^4$=H, n=1, $R^5$=H and X=O is prepared.

The synthesis of the compound 3 starts with the reaction of the commercially available 1-fluoro-4-nitrobenzene with the also commercially available piperidine-2-methanol to the intermediate product (1) ((1-(4-nitrophenyl)piperidine-2-yl)methanol).

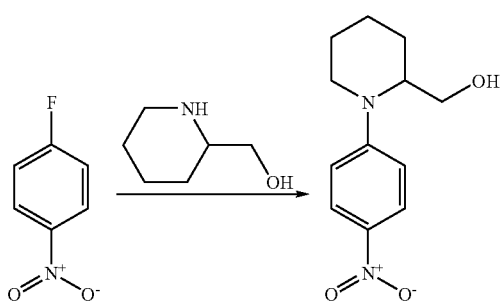 (1)

The obtained intermediate product (1) is then esterified with methacrylic chloride to the compound 4.

The parameter values specified in the documents for defining process and measurement conditions for the characterization of specific characteristics of the subject matter of the invention are also considered encompassed by the scope of the invention within the scope of deviations for example due to measurement errors, system errors, weighting errors, DIN tolerances and the like.

The invention claimed is:

1. An ophthalmologic composition including a dye wherein the dye has the structure

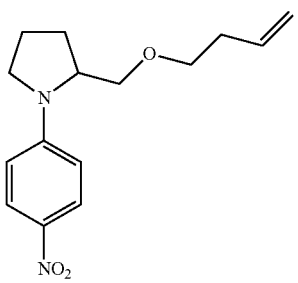 [SMILES: C=CCCOCC1CCCN1c1ccc([N+](=O)[O-])cc1]

and wherein the dye is covalently incorporated in a polymer.

2. The ophthalmologic composition according to claim 1, which includes a monomer according to the following general formula III (general formula III)

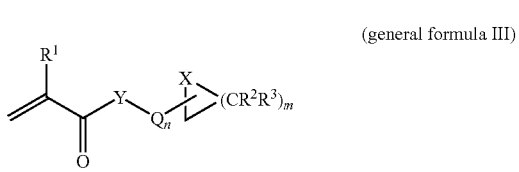

wherein
$R^1$, $R^2$ and $R^3$ each independently of each other denote hydrogen or alkyl,
Y: denotes O or NR$^4$ with R$^4$ selected from hydrogen or alkyl, X: denotes O, S, SO or $SO_2$, Q: denotes a structural unit selected from $CHR^5$ or $(CHR^5CHR^6O)_iCH_2$, wherein $R^5$ and $R^6$ each independently of each other denote hydrogen or alkyl, n and i independently of each other denote an integer between 1 and 10, and m denotes an integer between 2 and 6.

3. An ophthalmologic lens including the ophthalmologic composition according to claim 1.

4. The ophthalmologic lens according to claim 3, wherein the lens is formed as an intraocular lens or as a contact lens.

5. An ophthalmologic composition including a dye having the structure

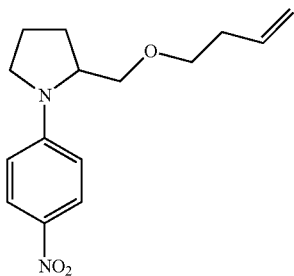

6. The ophthalmologic composition according to claim 5, which includes a monomer according to the following general formula III

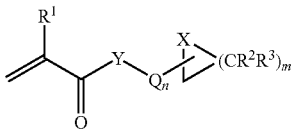

(general formula III)

wherein $R^1$, $R^2$ and $R^3$ each independently of each other denote hydrogen or alkyl, Y: denotes O or $NR^4$ with $R^4$ selected from hydrogen or alkyl, X: denotes O, S, SO or $SO_2$, Q: denotes a structural unit selected from $CHR^5$ or $(CHR^5CHR^6O)_iCH_2$, wherein $R^5$ and $R^6$ each independently of each other denote hydrogen or alkyl, n and i independently of each other denote an integer between 1 and 10, and m denotes an integer between 2 and 6.

7. The ophthalmologic composition according to claim 5, including:

50-90 HEMA;
10-40% MMA;
0.25-1.5% cross-linker;
0.01-0.3%, radical initiator;
0.1-3.0% UV absorber; and
0.02-0.3% dye.

8. An ophthalmologic lens including the ophthalmologic composition according to claim 5.

9. The ophthalmologic lens according to claim 8, wherein the lens is formed as an intraocular lens or as a contact lens.

\* \* \* \* \*